US00PP21204P2

(12) United States Plant Patent
Kolk

(10) Patent No.: US PP21,204 P2
(45) Date of Patent: Aug. 17, 2010

(54) *HYDRANGEA* PLANT NAMED 'LOLLY POP'

(50) Latin Name: *Hydrangea macrophylla*
Varietal Denomination: Lolly Pop

(76) Inventor: Jacobus W. P. Kolk, Legmeerdijk 210, 1187 NK Amstelveen (NL)

( * ) Notice: Subject to any disclaimer, the term of this patent is extended or adjusted under 35 U.S.C. 154(b) by 0 days.

(21) Appl. No.: 12/456,110

(22) Filed: Jun. 11, 2009

(51) Int. Cl.
*A01H 5/00* (2006.01)

(52) U.S. Cl. ..... Plt./250

(58) Field of Classification Search ..... Plt./250
See application file for complete search history.

(56) References Cited

OTHER PUBLICATIONS

Upov Plant Variety Database 2010/02 search for cultivar Lolly Pop p. 1.*

* cited by examiner

*Primary Examiner*—Annette H Para
(74) *Attorney, Agent, or Firm*—Penny J. Aguirre

(57) ABSTRACT

A new cultivar of *Hydrangea macrophylla* named 'Lolly Pop' that is characterized by its free-flowering habit and suitability as a cut flower, its well-developed mop-head type inflorescences with sterile flowers that are pink in color, held on sturdy pedicels, and resistant to sun scorch, high winds and rain and its very strong stems with sturdy leaves.

2 Drawing Sheets

Genus/species: *Hydrangea macrophylla.*
Varietal denomination: 'Lolly Pop'.

BACKGROUND OF THE INVENTION

The present invention relates to a new and distinct cultivar of *Hydrangea macrophylla* and will be referred to hereafter by its cultivar name, 'Lolly Pop'. 'Lolly Pop' represents a new Bigleaf *Hydrangea*, a deciduous shrub grown for landscape use and for use as for use as a cut flower.

'Lolly Pop' was derived from an ongoing controlled breeding program by the Inventor that focuses on developing new cultivars of bigleaf *hydrangeas* for cut flower use. 'Lolly Pop' originated from a cross conducted in the Inventor's nursery in June 1999 in Amstelveen, The Netherlands between *Hydrangea macrophylla* 'Bodensee' (not patented) as the female parent and *Hydrangea macrophylla* 'Snowball' (not patented) as the male parent. The new *Hydrangea* was selected as a unique single plant from the progeny of the cross in May 2003.

Asexual reproduction of the new cultivar was first accomplished by softwood stem cuttings in Amstelveen, The Netherlands in August 2003 by the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Lolly Pop' as a unique cultivar of *Hydrangea macrophylla.*

1. 'Lolly Pop' exhibits a free-flowering habit.
2. 'Lolly Pop' exhibits well-developed mop-head type inflorescences with sterile flowers that are pink in color.
3. 'Lolly Pop' exhibits very strong stems with sturdy leaves.

4. 'Lolly Pop' exhibits inflorescences that are sturdy with strong pedicels.
5. 'Lolly Pop' exhibits inflorescences that resistant to sun scorch, high winds and rain.
6. 'Lolly Pop' is suitable for use as a cut flower.
7. 'Lolly Pop' is hardy at least U.S.D.A. Zones 4 to 9.

The closest comparison plants to the new cultivar of *Hydrangea* are the parent plants. 'Bodensee' differs from 'Lolly Pop' in having much weaker stems, larger sized leaves, larger sized inflorescences, and sterile flowers that are lighter pink in color and subject to developmental abortion. 'Snowball' differs from 'Lolly Pop' having weaker stems, larger sized leaves, larger sized inflorescences, and inflorescences that are white in color and susceptible to sun scorch.

BRIEF DESCRIPTION OF THE DRAWINGS

The photographs in the figures were taken of a two year-old plant of 'Lolly Pop' as grown under greenhouse conditions with ambient light in a 3.5-liter container in Amstelveen, The Netherlands.

The photograph in FIG. 1 illustrates a side view of a plant of 'Lolly Pop' with fully mature to fading blooms.

Figure 1:
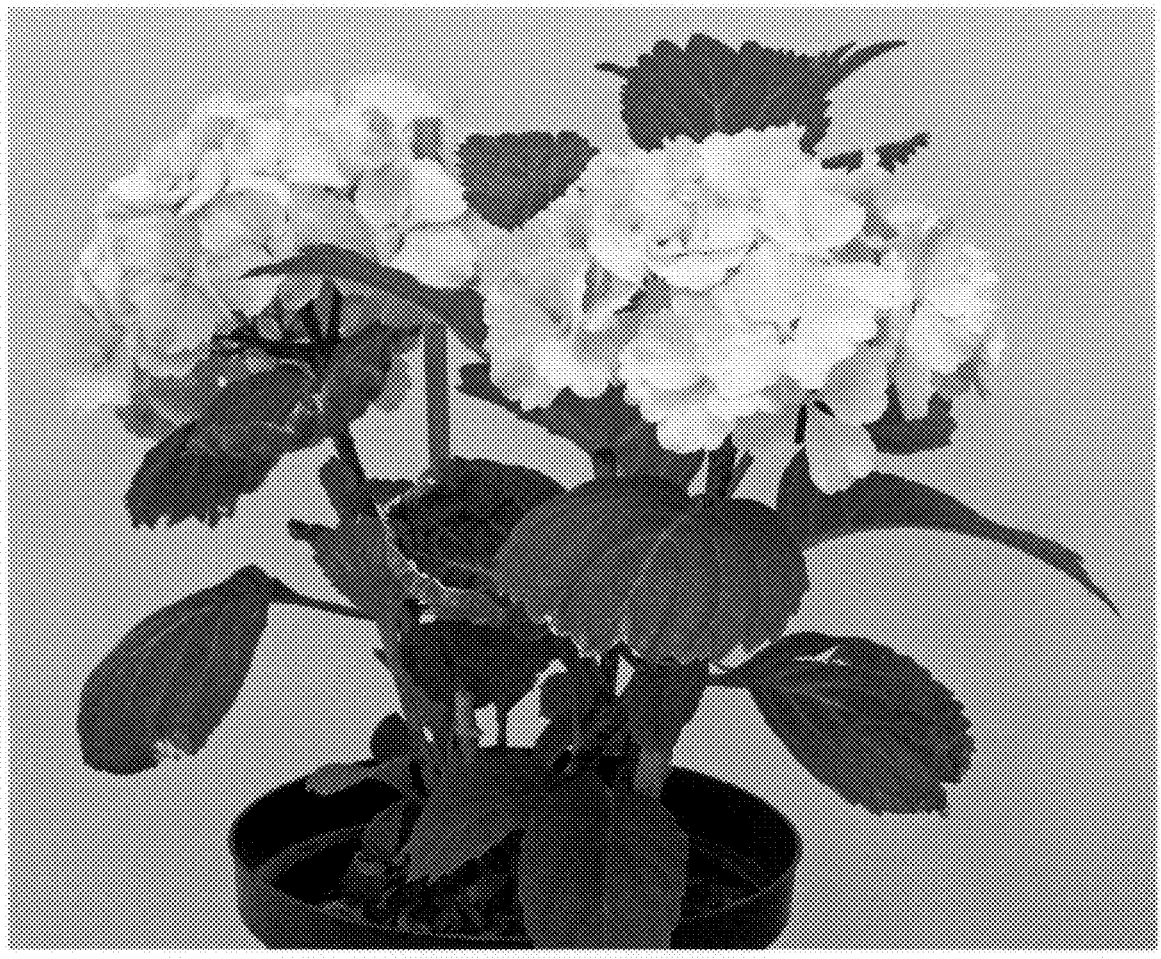
Figure 2:
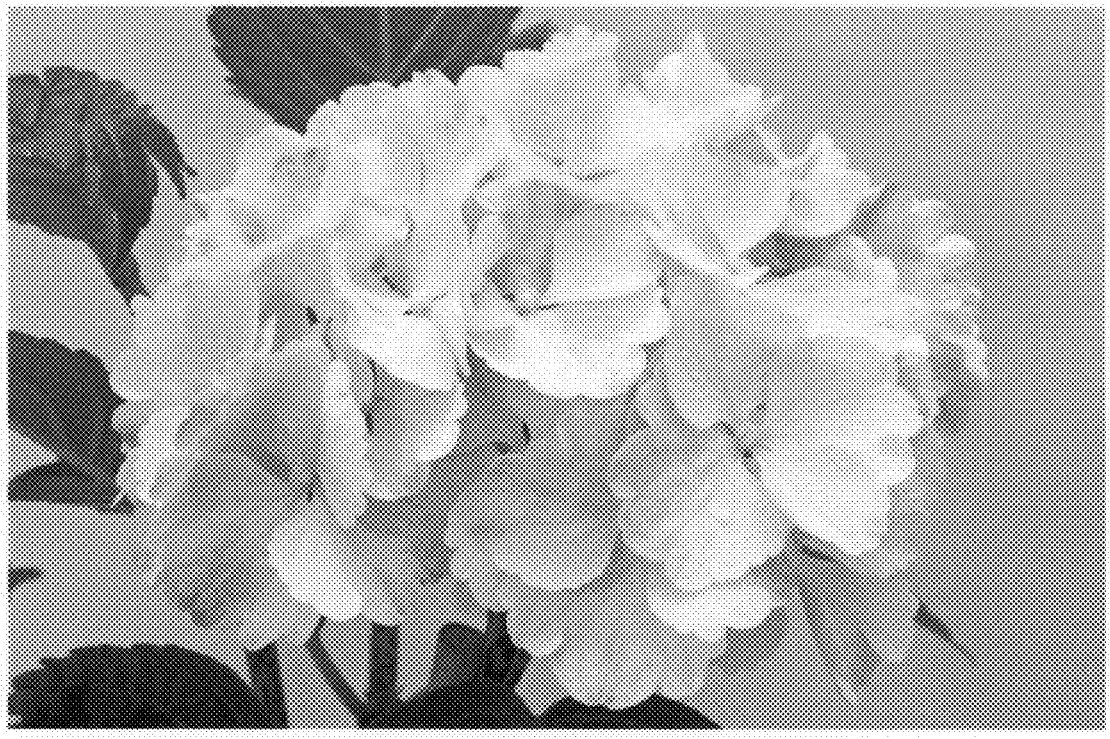

The photograph in FIG. 2 provides a close-up view of an inflorescence of 'Lolly Pop'.

Figure 3:
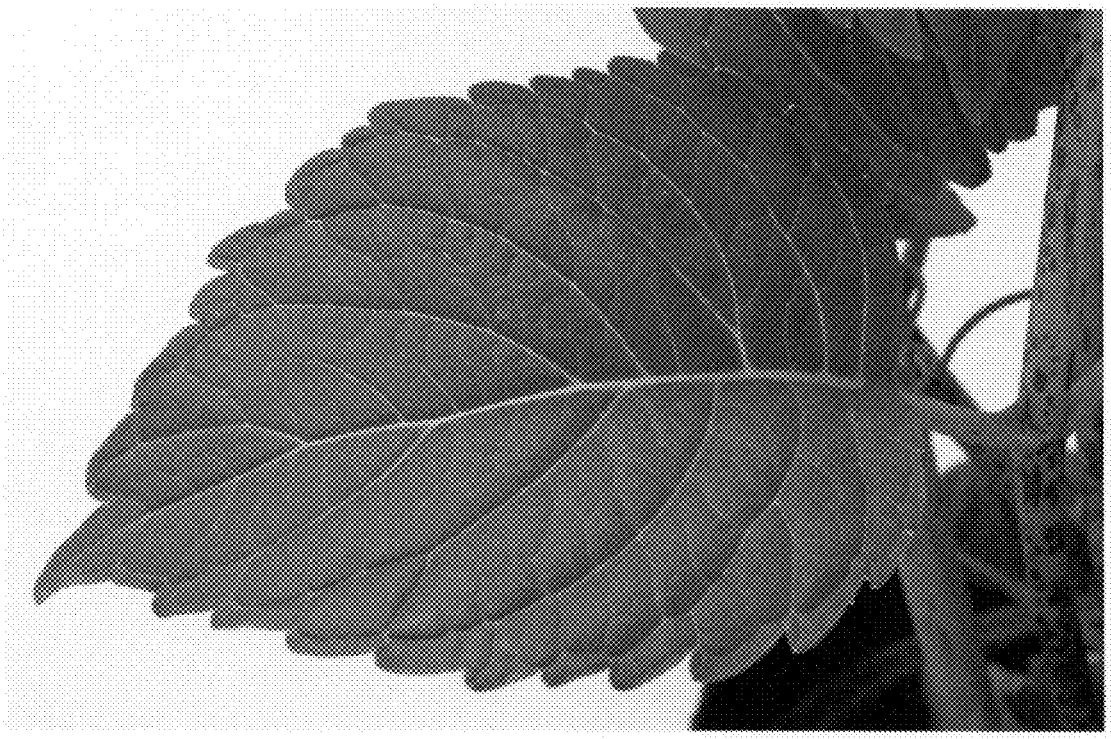

The photograph in FIG. 3 provides a close-up view of a leaf of 'Lolly Pop'. The colors in the photographs are as close as possible with the digital photography and printing techniques utilized and the color codes in the detailed botanical description more accurately describe the new *Hydrangea.*

BOTANICAL DESCRIPTION OF THE PLANT

The following is a detailed description of two year-old plants of 'Lolly Pop' as grown under greenhouse conditions with ambient light in a 3.5-liter container in Amstelveen, The Netherlands. The plants were grown under average day temperatures of 12 to 22° C. and average night temperatures of 8 to 18° C. Phenotypic differences may be observed with variations in environmental, climatic, and cultural conditions. The color determination is in accordance with the 2007 R.H.S .Colour Chart of The Royal Horticultural Society, London, England, except where general color terms of ordinary dictionary significance are used.

General description:

*Blooming period.*—Summer blooming.

*Plant habit.*—Broadly upright, deciduous shrub, sturdy.

*Height and spread.*—Reaches about 32.2 cm in height and 34.3 cm width.

*Hardiness.*—At least in U.S.D.A. Zones 4 to 9.

*Diseases resistance.*—No susceptibility or resistance diseases known to effect H. macrophylla has been observed.

*Root description.*—Fibrous, dense.

Growth and propagation:

*Propagation.*—Softwood stem cuttings.

*Time required for root development.*—About 4 weeks to fully develop in a liner as grown under greenhouse conditions at an average temperature of 20° C.

*Time required to produce a salable crop.*—About 12 months from propagation to a small saleable plant in a 2-liter container.

*Growth rate and vigor.*—Moderate.

Stem description:

*Stem shape.*—Round, smooth.

*Stem strength.*—Very strong.

*Stem color.*—Immature; N144D, densely covered with narrow oblong lenticels that are an average of 4 mm in length and 0.75mm in width and 183B in color, mature; 143C, densely covered with narrow oblong lenticels that are an average of 5 mm in length and 1 mm in width and 183A in color.

*Stem size.*—Average of 21 cm (to base of inflorescence) and average of 6 mm in width.

*Stem surface.*—Glabrous, semi-glossy.

*Branching.*—A single dormant stem will produce an average of 5 lateral branches, sublateral branching is determined by pinching; 2 stems develop per pinched node.

*Internode length.*—Average of 7.7 cm.

Foliage description:

*Leaf shape.*—Broadly ovate.

*Leaf arrangement.*—Opposite.

*Leaf division.*—Simple.

*Leaf number.*—Average of 6 (3 pairs) per lateral branch.

*Leaf base.*—Rounded to short attenuate.

*Leaf apex.*—Acute.

*Leaf margins.*—Serrated.

*Leaf venation.*—Pinnate, recessed on upper surface, color 144A on upper surface and 145C on lower surface.

*Leaf size.*—Average of 10.8 cm in length and 9.3 cm in width.

*Leaf attachment.*—Petiolate.

*Leaf surface.*—Dull on upper and lower surface, slightly rugose on upper surface.

*Leaf color.*—Young foliage upper surface; 141A to 141B, young foliage lower surface; 137D, mature foliage upper surface; N137C, mature foliage lower surface; 138B.

*Petioles.*—Average of 2.9 cm in length and 4 mm in width, color; upper side 144A, under side 144C to 145A, surface is smooth and slightly glossy.

Inflorescence description:

*Inflorescence type.*—Terminal compound flattened globose corymb of rotate-shaped sterile flowers above fertile flowers.

*Lastingness of inflorescence.*—Persistent with color lasting about 4 weeks.

*Inflorescence number.*—One per lateral or sublateral stem if pinched.

*Inflorescence size.*—Average of 12.2 cm in height and 15.9 cm in diameter.

*Flower number.*—An average of 100 sterile flowers and 35 fertile flowers per inflorescence.

*Flower durability to stress.*—Highly resistant to sun scorch, high winds and rain.

*Flower fragrance.*—None.

*Flower aspect.*—Upright to outward.

*Flower size.*—Sterile flowers; average of 8 mm in diameter and 1.2 cm in depth, fertile flowers; average of 5 mm in diameter and 3 mm in depth.

*Flower buds.*—Sterile flowers; an average of 1.2 mm in length and 2.8 mm in width prior to opening, ovate in shape, 157B to 157C in color, fertile flowers; an average of 3 mm in length and 5 mm in width prior to opening, flattened globular in shape, 158D in color.

*Peduncles.*—None, inflorescences at terminal of stem.

*Pedicels.*—Sterile flowers; strong, an average of 2.7 cm in length and 2 mm in width, held at an average angle of 45° , 75C to 75D in color, surface is dull and moderately covered with very short hairs 69D in color, fertile flowers; moderate strength, an average of 4 mm in length and 0.5 mm in width, held upright, 144D in color, surface is dull and moderately covered with very short hairs 157D in color.

*Petals.*—Sterile flowers; an average of 4, rotate in arrangement, broadly ovate in shape, entire margin, acute apex, cuneate base, average of 3 mm in length and 2 mm in width, surface is smooth and dull on both surfaces, color of upper surface (opening and mature flowers) is 69D, color of lower surface (opening and mature flowers) is 67C, fertile flowers; an average of 5, rotate in arrangement, broadly ovate in shape, entire margin, acute apex, cuneate base, average of 2.5 mm in length and 1.5 mm in width, surface is smooth and dull on both surfaces, color of upper surface when opening N155B, when mature N155C, color of lower surface when opening N155C to N155D, when mature N155C.

*Sepals.*—Sterile flowers; average of 4 flowers, rotate in arrangement, glabrous and dull surface (both surfaces), orbicular to reniform in shape, margin is entire on lower ⅓ is crenate on upper ⅔, apex is obtuse, an average of 2.7 cm in length and 3.1 cm in width, color when opening; upper surface 69B to 69C and lower surface 69C, color upper when fully open; upper surface 73C to 73D blended with 69B towards apex, lower surface 73C to 73D blending to 69B towards apex with apex tinged with 145C, color when fading; upper and lower surface 69B with upper half 145C.

Reproductive organs:

*Presence.*—Sterile flowers; eye is comprised of a fertile flower with deformed stamens, fertile flowers; all organs are deformed.

*Stamens.*—Sterile flowers; 4, deformed, filament is an average of 1 mm in length and 145D in color, anther is an average of 0.5 mm in length and 157A in color, no pollen was observed, fertile flowers; too deformed for description.

*Pistils.*—Sterile flowers; 1, about 1.2 mm in length, style is about 1.7 mm in length and 145A to 145B in color, stigma is flattened club-shaped and 155D in color, ovary is 145A to 145B in color, fertile flowers; 1, deformed, about 1.5 mm in length, stigma is flattened club-shaped and 157B to 157C in color, ovary is 145D in color.

*Fruit and seed.*—Has not been observed under the conditions tested to date.

It is claimed:

1. A new and distinct cultivar of *Hydrangea* plant named 'Lolly Pop' substantially as herein illustrated and described.

* * * * *